United States Patent
Adams et al.

(10) Patent No.: US 6,527,747 B2
(45) Date of Patent: *Mar. 4, 2003

(54) INTRODUCER NEEDLE ASSEMBLY HAVING A TETHERED NEEDLE SHIELD

(75) Inventors: Chad Michael Adams, West Jordan, UT (US); William Gary Moulton, West Jordan, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/865,761

(22) Filed: May 25, 2001

(65) Prior Publication Data

US 2002/0177813 A1 Nov. 28, 2002

(51) Int. Cl.[7] ................................................ A61M 5/32
(52) U.S. Cl. ........................ 604/162; 604/198; 604/171
(58) Field of Search .................................. 604/162, 163, 604/164.01, 164.07, 164.08, 164.09, 187, 192, 198, 263, 171

(56) References Cited

U.S. PATENT DOCUMENTS

| | | | | | |
|---|---|---|---|---|---|
| 4,725,267 A | * | 2/1988 | Vaillancourt | ................ | 604/192 |
| 4,790,828 A | * | 12/1988 | Dombrowski et al. | ...... | 604/110 |
| 4,846,809 A | * | 7/1989 | Sims | ........................ | 604/198 |
| 4,935,013 A | * | 6/1990 | Haber et al. | ................ | 604/192 |
| 4,955,866 A | * | 9/1990 | Corey | ........................ | 604/192 |
| 4,978,344 A | * | 12/1990 | Dombrowski et al. | ...... | 604/198 |
| 5,051,109 A | * | 9/1991 | Simon | ........................ | 604/192 |
| 5,059,180 A | * | 10/1991 | McLees | ...................... | 604/110 |
| 5,348,544 A | * | 9/1994 | Sweeney et al. | ............ | 128/919 |
| 5,419,766 A | * | 5/1995 | Chang et al. | ............... | 604/110 |
| 5,447,501 A | * | 9/1995 | Karlsson et al. | ............ | 600/576 |
| 5,478,313 A | * | 12/1995 | White | ........................ | 604/110 |
| 5,549,571 A | * | 8/1996 | Sak | ............................. | 128/919 |
| 5,562,633 A | * | 10/1996 | Wozencroft | ................. | 604/171 |
| 5,569,202 A | * | 10/1996 | Kovalic et al. | ............. | 604/110 |
| 5,685,860 A | * | 11/1997 | Chang et al. | ............... | 604/192 |
| 5,879,337 A | * | 3/1999 | Kuracina et al. | ........... | 604/192 |
| 5,910,132 A | * | 6/1999 | Schultz | ...................... | 604/162 |
| 5,957,892 A | * | 9/1999 | Thorne | ....................... | 604/162 |
| 5,980,488 A | | 11/1999 | Thorne | ....................... | 604/110 |
| 6,234,999 B1 | * | 5/2001 | Wemmert et al. | .......... | 604/162 |

* cited by examiner

Primary Examiner—Manuel Mendez
Assistant Examiner—Mark Han
(74) Attorney, Agent, or Firm—James J. Murtha

(57) ABSTRACT

A catheter and introducer needle assembly with needle shield that is connected to the needle hub by a pleated tether. The tether defines a plurality of holes therein to allow the introducer needle to extend through the tether. Each hole defines a longitudinal dimension and a radial dimension such that the radial dimension is less than the longitudinal dimension. This configuration improves the tensile strength of the tether. The tether prevents unwanted proximal movement of the needle with respect to the needle shield once the needle has been withdrawn into the needle shield.

14 Claims, 13 Drawing Sheets

INTRODUCER NEEDLE ASSEMBLY HAVING A TETHERED NEEDLE SHIELD

BACKGROUND OF THE INVENTION

The subject invention relates to an introducer needle assembly for use with a catheter, where the introducer needle assembly includes a tethered needle shield that will safely shield the sharp distal tip of the introducer needle after the needle has been used to insert the catheter into a patient.

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel. These are smaller blood vessels that are not connected directly to the heart but are the branches of the central blood vessels that are directly connected to the heart. In order to verify proper placement of the assembly in the blood vessel, the clinician confirms that there is flashback of blood in the needle and in a flashback chamber located at the proximal end of the needle. The flashback chamber is typically formed as part of the needle hub. Once proper placement is confirmed, the clinician applies pressure to the blood vessel by pressing down on the patient's skin over the distal tip of the introducer needle and the catheter. This finger pressure occludes further blood flow through the introducer needle. The clinician withdraws the introducer needle, leaving the catheter in place, and attaches a fluid-handling device to the catheter hub.

Once the introducer needle is withdrawn from the catheter, it is a "blood contaminated sharp" and must be properly handled. In recent years, there has been great concern over the contamination of clinicians with a patient's blood and a recognition that "blood contaminated sharps" must be immediately disposed. This concern has arisen because of the advent of currently incurable and fatal diseases, such as Acquired Immune Deficiency Syndrome ("AIDS") and hepatitis, which can be transmitted by the exchange of body fluids from an infected person to another person. Thus, contact with the body fluid of an AIDS or hepatitis infected person must be avoided to prevent the transmission of such diseases to a healthy person. As noted above, if an introducer needle has been used to place a catheter in the vein of an AIDS or hepatitis infected person, the introducer needle is a vehicle for the transmission of the disease. Although clinicians are aware of the need to properly handle "blood contaminated sharps", unfortunately in certain medical environments, such as emergency situations or as a result of inattention or neglect, needlesticks with contaminated introducer needles still occur.

As a result of the problem of accidental needlesticks by "blood contaminated sharps", various needle shields have been developed. Generally, such needle shields work for their intended purpose but could be improved. For example, some needle shields are not positively connected to the introducer needle assembly and could be advanced distally past the distal end of the introducer needle. In addition, some introducer needle assemblies having a needle shield associated therewith are bulky, difficult to use or require special features or techniques to be operative or are ergonomically uncomfortable for the clinician to use.

SUMMARY OF THE INVENTION

It is therefore an object of this invention to provide an introducer needle assembly having a needle shield that is positively connected to the introducer needle assembly to prevent the needle shield from being advanced distally past the distal end of the introducer needle.

It is another object of this invention to provide an introducer needle assembly with a needle shield that is compact.

It is yet another object of this invention to provide an introducer needle assembly with a needle shield that is simple and easy to use.

It is still another object of this invention to provide an introducer needle assembly with a needle shield that requires no special features or technique to be operative.

It is a further object of this invention to provide an introducer needle assembly with a needle shield that is ergonomically comfortable for the clinician to use.

The catheter and introducer needle assembly of this invention includes a needle shield connected to the needle hub by a tether. The introducer needle has a sharp distal tip and a proximal end connected to the distal end of a needle hub. A flashback chamber is defined in the needle hub. A vented plug may be located in the open proximal end of the flashback chamber to allow air to escape from the flashback chamber when blood enters the flashback chamber from the introducer needle. The catheter, which has a distal end and a proximal end connected to the distal end of a catheter adapter, is coaxially disposed over the introducer needle so the sharp distal tip of the introducer needle is distal of the distal end of the catheter.

The needle shield is located substantially between the catheter and the needle hub and defines a longitudinally extending passage through which the introducer needle extends. The needle shield may include some barrier or other mechanism that prevents the sharp distal tip of the needle from being moved distally with respect to the needle shield after the sharp distal tip of the needle has been withdrawn into the needle shield. This prevents the sharp distal tip of the needle from being reexposed once it has been withdrawn into the needle shield.

The needle shield is connected to the needle hub by a tether that prevents the needle shield from being moved distally past the sharp distal tip of the needle once the needle has been proximally withdrawn into the needle shield. The combination of the barrier or other mechanism associated with the needle shield and the tether prevents distal movement of the needle with respect to the needle shield. This ensures that the sharp distal tip of the needle remains trapped in the needle shield after the needle has been withdrawn proximally into the needle shield after use.

The tether is folded over itself to form a plurality of pleats like an accordion. Each pleat or fold defines a central opening therein to allow the needle to extend through each pleat or fold no matter whether the tether is completely extended or completely folded with the needle shield adjacent to the needle hub. Each opening has a configuration where the radial dimension of the opening is smaller than the longitudinal dimension of the opening. For example, each opening can have a generally race track configuration, an elliptical configuration or a generally rectangular configuration. Because the tether can be folded into a small space so it is located between the needle shield and the needle hub, the overall device is compact. This makes the overall device easier to control by the clinician. In addition, the pleated configuration of the tether allows the clinician to better control the action of the needle shield. The tether is connected to the needle hub and the needle shield by a variety of mechanisms, such as by an adhesive, by heat-sealing or by mechanical engagement.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
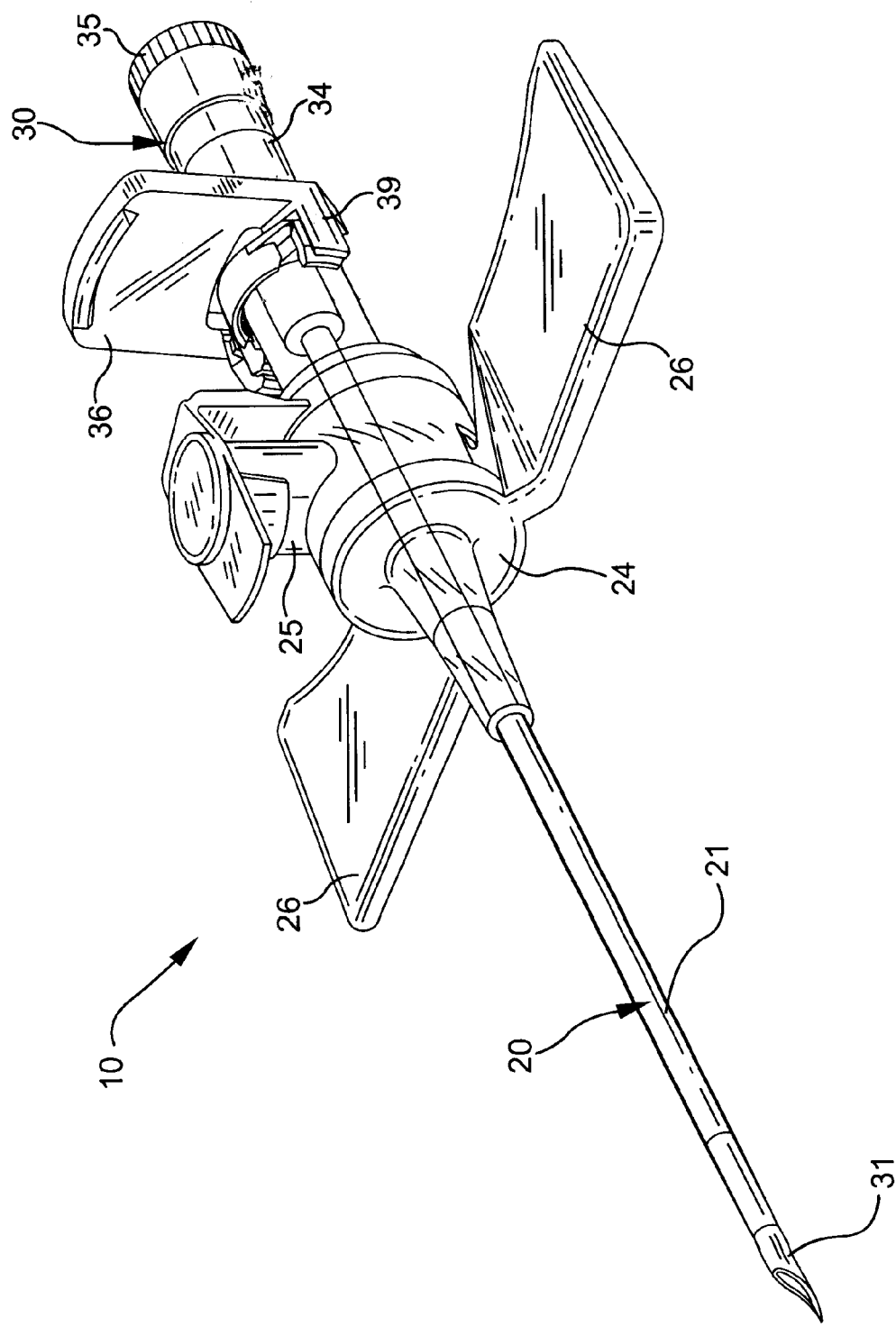
FIG. 1 is a perspective view of a ported catheter and introducer needle assembly including the tether of this invention prior to use.
Figure 2:
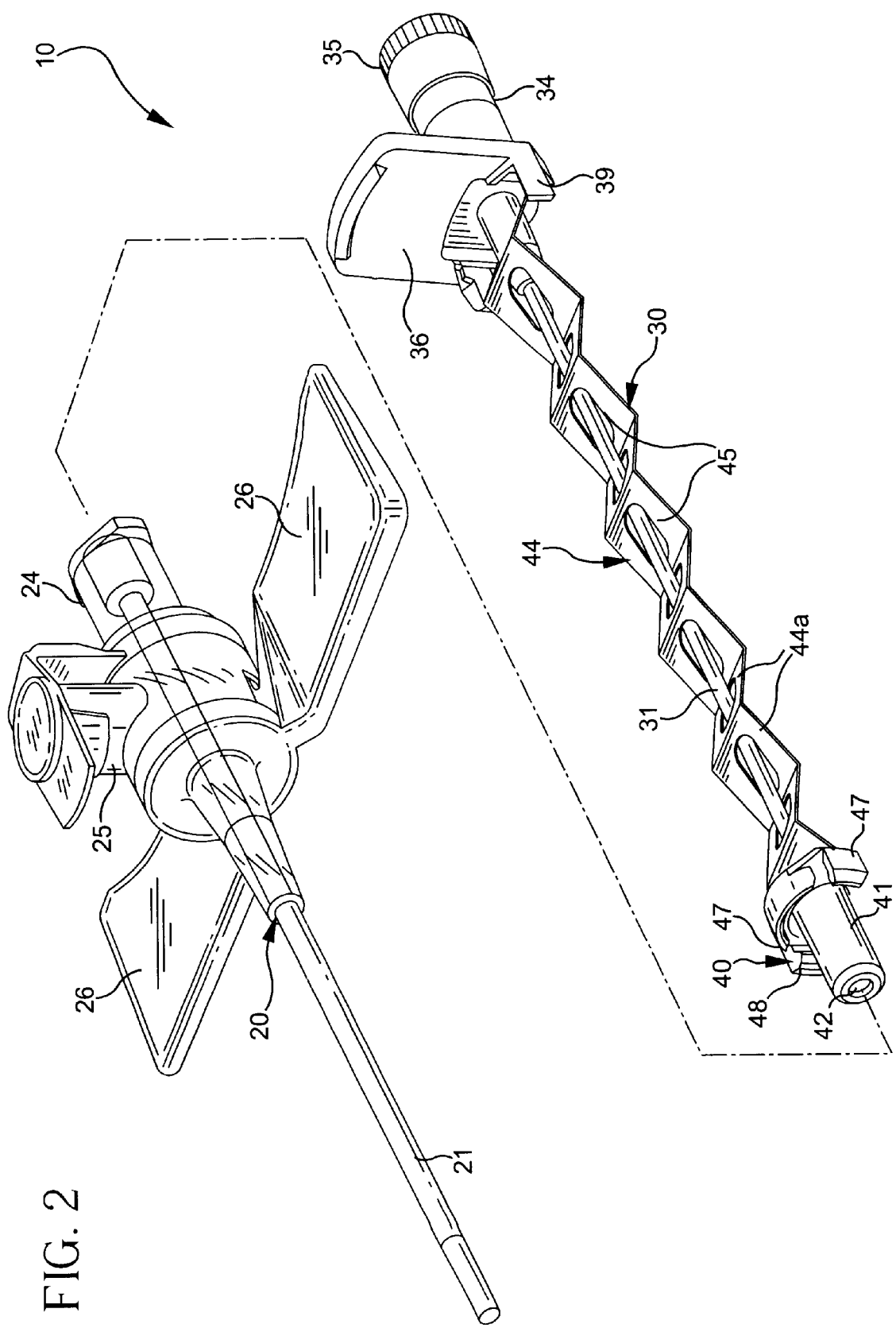
FIG. 2 is a perspective view of a ported catheter and introducer needle assembly including the tether of this invention after the needle has been withdrawn from the catheter into the needle shield and the needle shield has been removed from the catheter adapter.

As used herein, the term "proximal" refers to a location on the device that is closest to the clinician using the device and farthest from the patient in connection with whom the device is used when the device is used in its normal operation. Conversely, the term "distal" refers to a location on the device that is farthest from the clinician using the device and closest to the patient in connection with whom the device is used when the device is used in its normal operation.

As used herein, the term "top", "up" or "upwardly" refers to a location with respect to the device that, during normal use, is radially away from the longitudinal axis of the device and away from the patient's skin. Conversely, as used herein, the term "bottom", down" or "downwardly" refers to a location with respect to the device that, during normal use, is radially away from the longitudinal axis of the device and toward the patient's skin.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

The catheter and introducer needle assembly of this invention is identified generally by the numeral 10. It includes a catheter assembly 20 and an introducer needle assembly 30 that includes a needle shield 40 and a tether 44.

Catheter assembly 20 includes a catheter 21 that has a proximal end and a distal end. A catheter adapter 24 is affixed to the proximal end of catheter 21. Suitable materials for catheter 21 include, but are not limited to, thermoplastic resins such as polytetrafluoroethylene (PTFE), fluorinated ethylene propylene copolymer (FEP), polyurethane and the like. Preferably, catheter 21 is formed from thermoplastic hydrophilic polyurethane that softens with exposure to physiological conditions present in the patient's body. Suitable materials for catheter adapter 24 include, but are not limited to, thermoplastic polymeric resins such as polycarbonate, polystyrene, polypropylene and the like.

Catheter adapter 24 may include a radially outwardly extending side port 25, which is useful for connecting a fluid handling device to catheter 21 for infusing fluids into the patient's blood vessel. See FIG. 1. Preferably, side port 25 extends upwardly away from the patient when catheter 21 is inserted into the patient. In addition, a pair of wings 26 may be attached to or integrally formed with catheter adapter 24. Wings 26 are useful to stabilize catheter 21 in the patient and provide a surface that facilitates taping of catheter assembly 20 to the patient to fix catheter 21 properly in the patient's vasculature.

Figure 9:
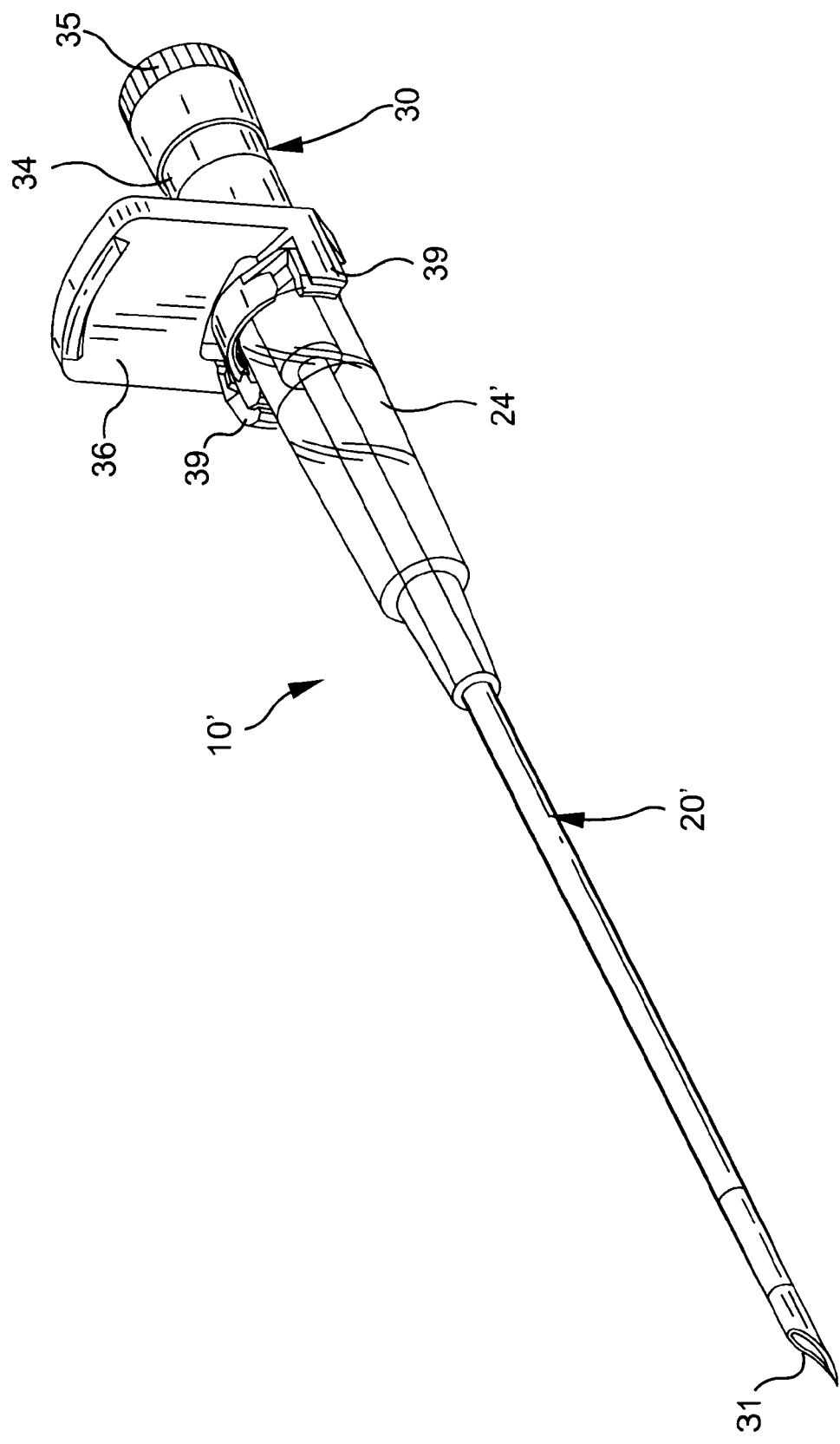
FIG. 9 is a perspective view of a straight catheter and introducer needle assembly including the tether of this invention prior to use.

Although, the majority of the description of catheter and introducer needle assembly 10 of this invention is directed to a catheter having a side port, it is to be understood that this invention can also be used with a straight catheter. See for example, FIG. 9.

A cover 27 may be used to cover catheter 21 and the introducer needle 31 prior to use. Preferably cover 27 is formed from a hard polymeric material such as thermoplastic polymeric resins, which include polycarbonate, polystyrene, polypropylene and the like. Of course other materials may also be used for cover 27.

Introducer needle assembly 30 includes introducer needle 31 having a sharp distal tip defined by a bevel. The proximal end of introducer needle 31 is connected to a needle hub 34. Introducer needle 31 is preferably formed from stainless steel. Needle hub 34 can include an integrated flashback chamber having an open proximal end. Needle hub 34 is preferably formed from the same types of materials that are used to form catheter adapter 24. Preferably, the open proximal end of needle hub 34 is closed to fluid flow by a vented plug 35 which allows air but not fluid to flow therethrough. This facilitates blood flow into the flashback chamber but prevents blood from leaking out.

Vented plug 35 may be removably connected to the open proximal end of needle hub 34. This allows a clinician to gain access to the patient's blood vessel during venipuncture. In this way, a syringe could be attached to the open proximal end of needle hub 34 for aspiration during insertion of catheter and introducer needle assembly 10.

Needle hub 34 may also include a radially extending tab 36, which may be grasped in combination with side port 25 to facilitate insertion of assembly 10 into the patient. Tab 36 may also be useful for withdrawing introducer needle 31 from catheter 21 after catheter 21 has been properly located in the patient's vasculature.

In addition, needle hub 34 may include a pair of longitudinally extending fingers 39. These fingers 39 frictionally engage needle shield 40. In this way, needle hub 34 is held in place adjacent to catheter hub 24 so that the sharp distal tip of introducer needle 31 extends distally of the distal end of catheter 21. The proximally directed force needed to overcome the frictional engagement between fingers 39 and needle shield 40 is less than the proximally directed force needed to overcome the removable connection between needle shield 40 and catheter adapter 24.

As noted above, introducer needle assembly 30 also includes needle shield 40. Like catheter adapter 24 and needle hub 34, suitable materials for needle shield 40 include, but are not limited to, thermoplastic polymeric resins such as polycarbonate, polystyrene, polypropylene and the like. Needle shield 40 includes main body portion 41, which defines a longitudinally extending passage 42 therethrough. Longitudinally extending passage 42 allows introducer needle 31 to extend longitudinally through main body portion 41. The diameter of longitudinally extending passage 42 is slightly larger than the diameter of the main portion of introducer needle 31. This allows the main portion of introducer needle 31 to easily pass through longitudinally extending passage 42.

An annular lip 43 is located along the distal portion of longitudinally extending passage 42. Preferably, lip 43 is integrally formed with needle shield 40 and contacts the main portion of introducer needle 31. In this way, lip 43 acts as a fluid seal along the main portion of introducer needle 31. During venipuncture, blood flow between introducer needle 31 and needle shield 40 is minimized to minimize blood leakage from the device.

A transverse barrier 49 may be located in needle shield 40 to act as a barrier against reexposure of the sharp distal tip of introducer needle 31 after it has been withdrawn into main body portion 41. Transverse barrier 49 is preferably formed as an integral member from a resilient metal, such as stainless steel. Preferably, transverse barrier is formed as a generally cylindrical main body portion 49b with two lips 49a in the configuration of a duckbill extending generally proximally from the distal end of main body portion 49b. The longitudinal dimension of main body portion 49b and lips 49a can be any value but preferably, main body portion 49b is longer than lips 49a. This relationship facilitates the manufacture of this device and makes for a more robust design.

Figure 7:
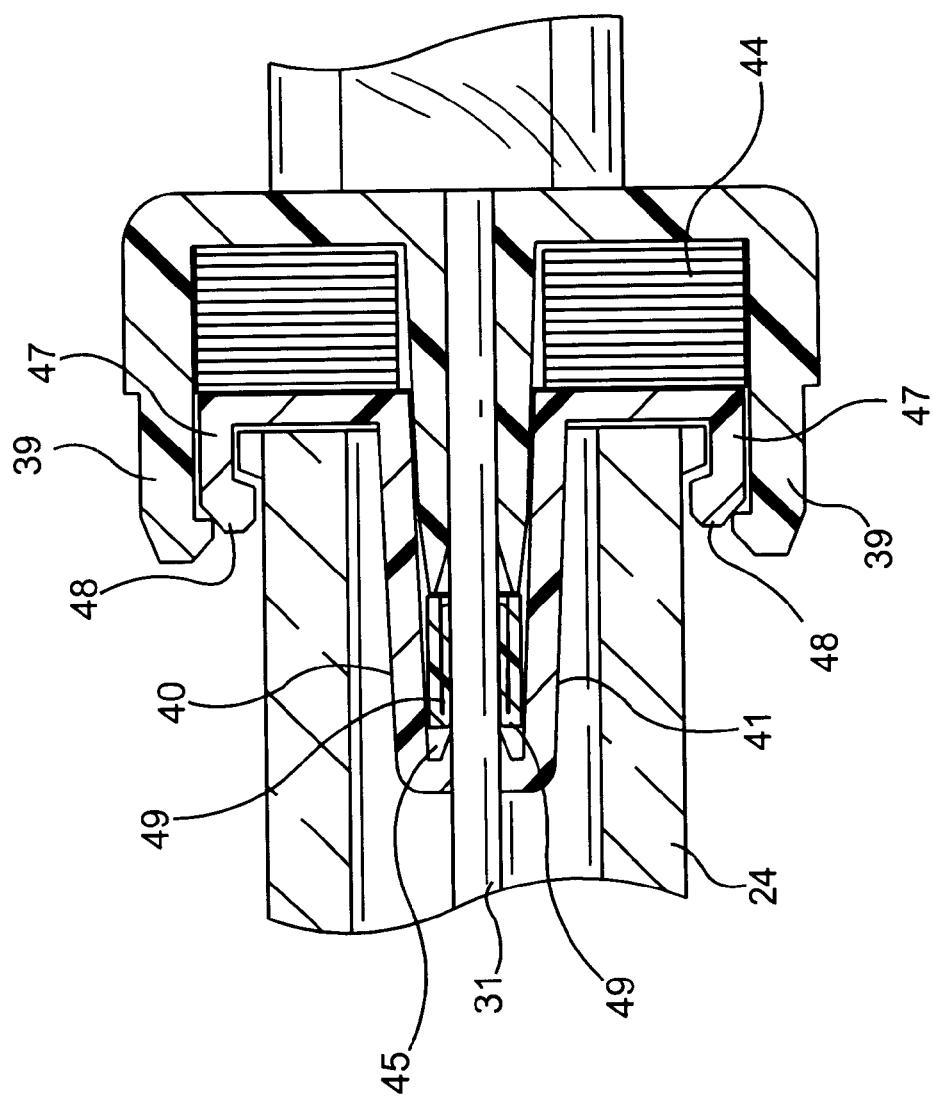
FIG. 7 is a cross sectional view of a portion of the introducer needle assembly showing the needle shield and tether prior to use and attached to a catheter adapter.
Figure 8:
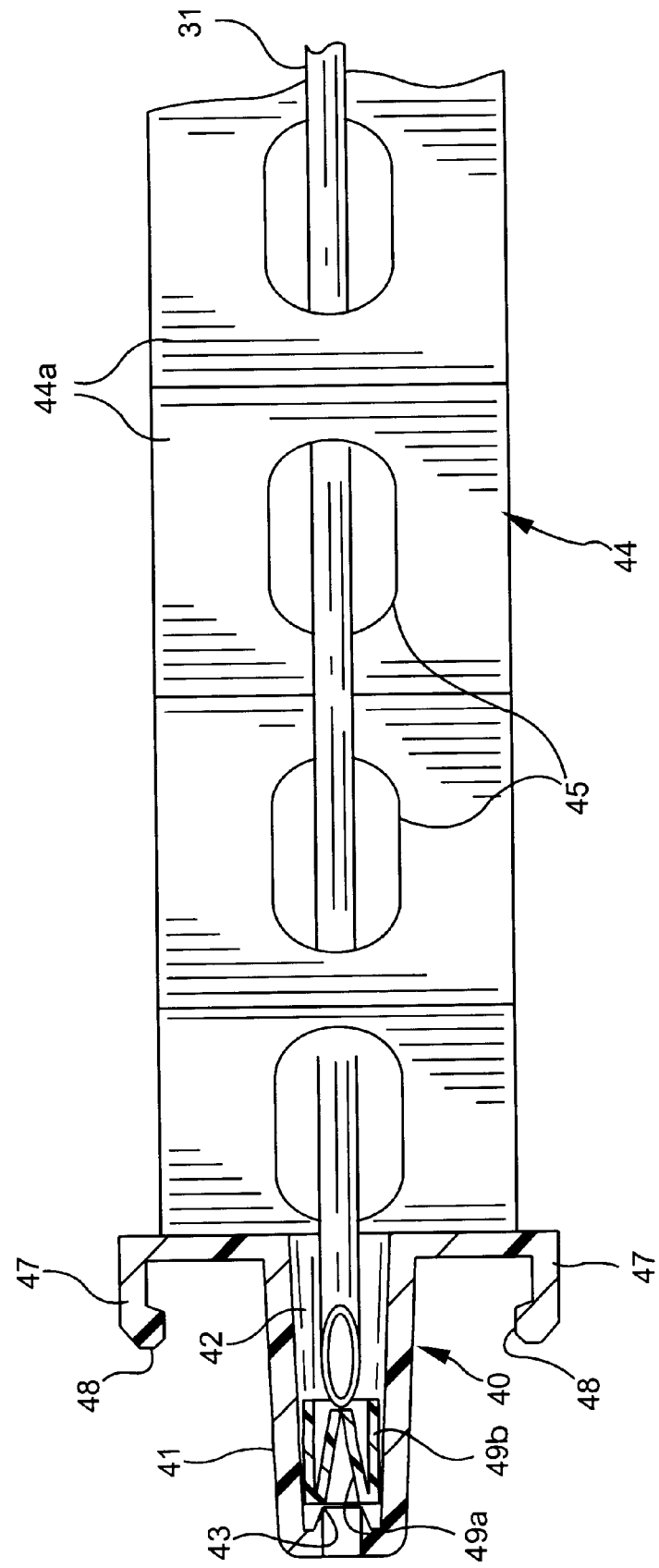
FIG. 8 is a cross sectional view of a portion of the introducer needle assembly showing the needle shield and tether after the sharp distal tip of the introducer needle has been withdrawn into the needle shield and the needle shield has been removed from the catheter adapter.

Prior to use, lips 49a extend toward the proximal end of introducer needle 31 and generally parallel to the main body portion of introducer needle 31. See FIG. 7. After proper placement of catheter 21 into a patient's blood vessel, lips 49a ride along the main body portion of introducer needle 31 when introducer needle 31 is being withdrawn from catheter 21. Once the sharp distal tip of introducer needle 31 is withdrawn to a position proximal of lips 49a, the resilient nature of lips 49a causes them to return to a position that is transverse to introducer needle 31. The configuration of lips 49a as shown in FIG. 8 prevents reexposure of the sharp distal tip that could occur if introducer needle 31 were thereafter moved distally with respect to needle shield 40. See FIG. 8.

Other types of transverse barriers could also be used. For example, a transverse barrier having a single arm could be used in place of the pair of lips 49a forming a duckbill as described above.

Main body portion 41 also includes a plurality of longitudinally extending fingers 47. Fingers 47 engage catheter adapter 24 to hold introducer needle assembly 30 together with catheter assembly 20. Thus, as needle hub 34 is moved proximally with respect to catheter adapter 24, needle shield 40 remains adjacent to catheter adapter 24. As described in more detail below, tether 44 has a length that maintains the sharp distal tip of introducer needle 31 in main body portion 41 of needle shield when tether 44 is fully extended. Thus, once the sharp distal tip of introducer needle 31 is moved into main body portion 41 of needle shield 40, any additional proximally directed movement applied to needle hub 24 will overcome the friction force between fingers 47 and catheter adapter 24. In this way, needle shield 40 can be removed from catheter adapter 24. If desired, main body portion 41 may be configured so that the exterior surface of the distal portion of main body portion 41 frictionally engages the interior surface of catheter adapter 24 to help hold needle shield 40 with catheter adapter 24.

Fingers 47 may also include radially inwardly directed projections 48. Projections 48 are sized to mechanically engage catheter adapter 24 by a snap fit. If projections 48 are used, the force needed to remove main body portion 41 from catheter adapter 24 may be more precisely controlled than if only fingers 47 or a friction fit are used. Once the proper proximally directed force is applied to main body portion 41, projections 48 override catheter adapter 24 and main body portion 41 can be removed from catheter adapter 24. Again, tether 44 maintains main body portion 41 in the proper location so that the sharp distal tip of introducer needle 31 is safely located within main body portion 41 of needle shield 40.

Tether 44 has a length that is comparable to the exposed length of introducer needle 31. This length maintains the sharp distal tip of introducer needle 31 in main body portion 41 of needle shield 40 when tether 44 is fully extended.

Figure 3:
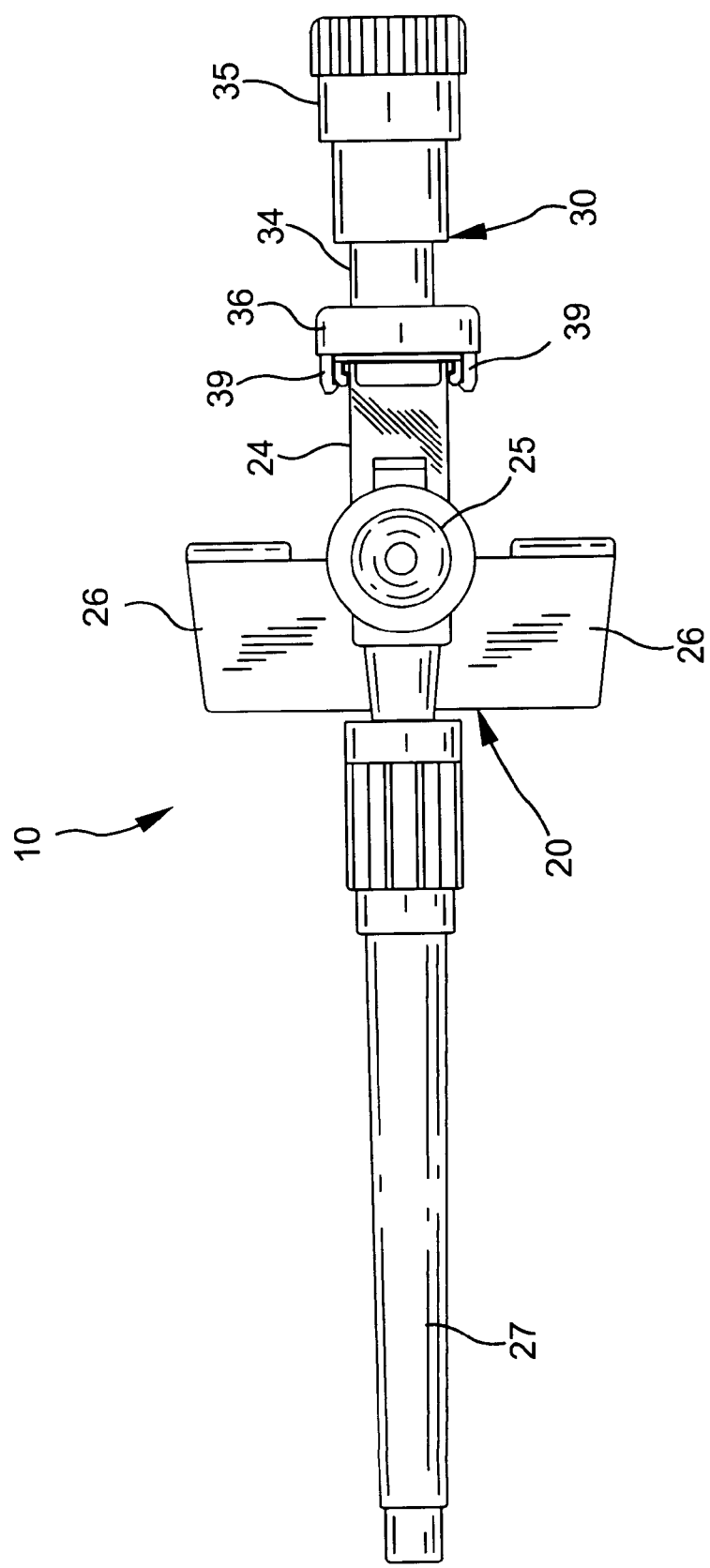
FIG. 3 is a top plan view of a ported catheter and introducer needle assembly including the tether of this invention prior to use.
Figure 4:
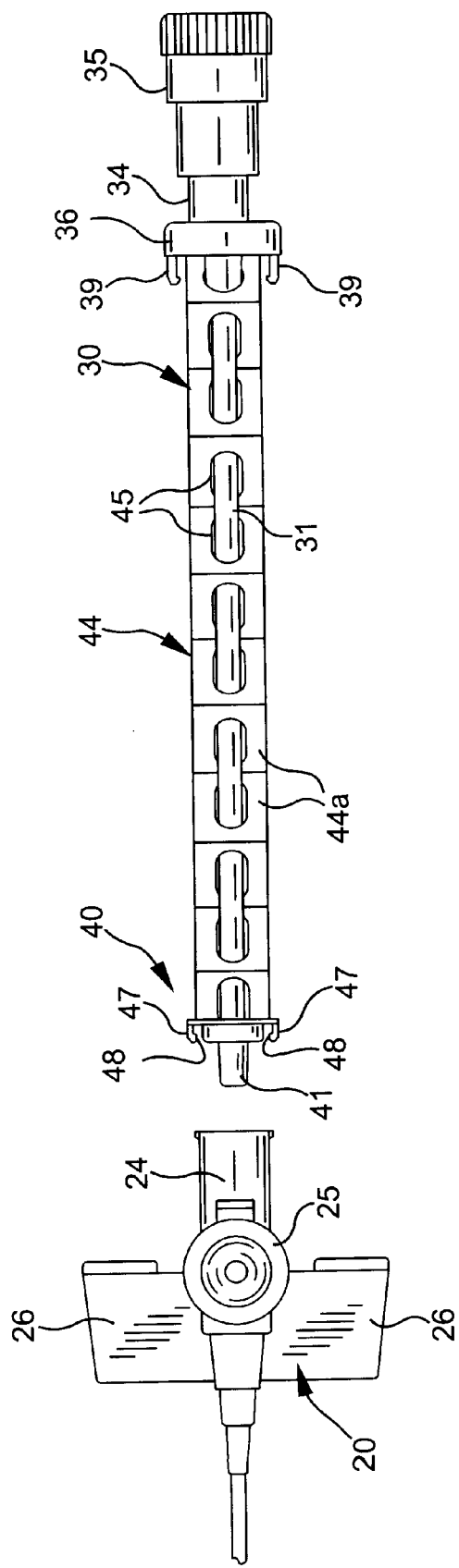
FIG. 4 is a top plan view of a ported catheter and introducer needle assembly including the tether of this invention after the needle has been withdrawn from the catheter into the needle shield and the needle shield has been removed from the catheter adapter.

Tether 44 is folded over itself to form a plurality of pleats 44a like an accordion. Each pleat 44a defines a central opening 45 therein to allow introducer needle 31 to extend through each pleat 44a whether tether 44 is completely extended, see FIG. 4, or completely folded with main body portion 41 of needle shield 40 adjacent to needle hub 34, see FIGS. 3 and 7. By forming tether 44 in this way, a compact design is achieved for catheter and introducer needle assembly 10.

Tether 44 can be made of any relatively stiff yet flexible material. However, polyethylene terephthalate (PET) is the preferred material. One benefit of using PET is that it is relatively stiff so that when it is folded into a pleated or an accordion-like configuration, it provides a slight biasing force to help maintain tether 44 in the completely extended position. This in turn aids in maintaining needle shield 40 in position over the sharp distal tip of introducer needle 31.

Figure 14:
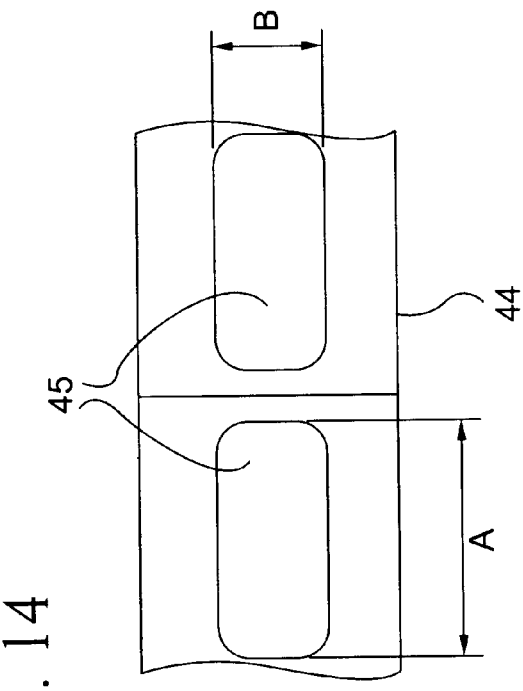
FIG. 14 is a top plan view of the tether of this invention showing openings in the tether that have a generally rectangular configuration.
Figure 13:
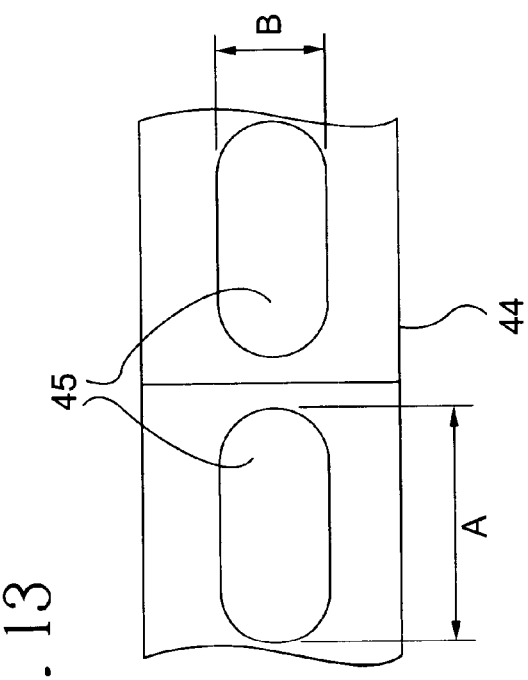
FIG. 13 is a top plan view of the tether of this invention showing openings in the tether that have a racetrack configuration.
Figure 15:
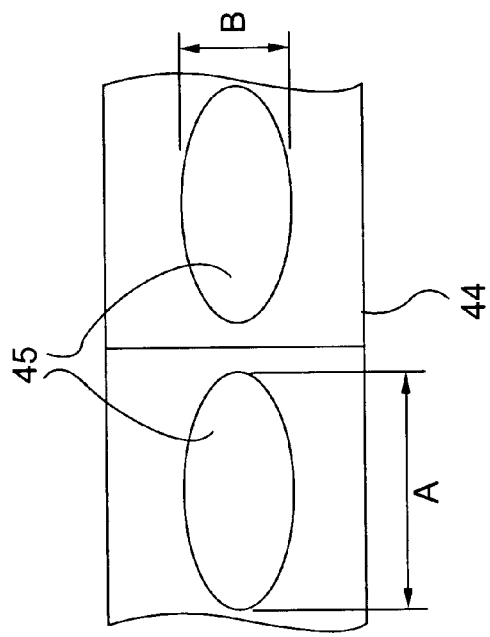
FIG. 15 is a top plan view of the tether of this invention showing openings in the tether that have an elliptical configuration.

Each opening 45 in pleats 44a should be of the smallest size practicable to allow introducer needle 31 to extend therethrough. By forming each opening 45 accordingly, a sufficient amount of the material forming tether 44 extends between adjacent openings 45 and between each opening 45 and the nearest edge to tether 44. In this way, the tensile strength of tether 44 is not compromised. Preferably, the configuration of each opening 45 is such that the longitudinal dimension A is greater than the radial dimension B. See, e.g. FIGS. 13–15. This configuration can take the specific form of a racetrack, i.e. where the sides of each opening 45 are straight and are joined by a curved surface at both ends. See FIG. 13. Alternatively, each opening 45 can have an elliptical configuration. See FIG. 14. Each opening 45 could also be generally rectangular. See FIG. 15. In addition, each opening 45 could have a different specific shape so long as the shape is narrower in the radial direction than it is in the longitudinal direction. As an example, each opening 45 as shown in FIG. 13 could have a radial dimension of 0.108 inches and a longitudinal dimension of 0.138 inches. With these dimensions, tether 44 should be 0.250 inches wide and preferably 0.0014 inches thick. Openings 45 should be aligned along the longitudinal axis of tether 44 and should be about 0.030 inches apart with the center to center distance between each opening 45 about 0.250 inches apart. When openings 45 are formed with this type of configuration, the tensile strength of tether 44 improves by over 36% as compared to a tether having openings in with a circular configuration where each circle has a diameter of about 0.14 inches. About half of this improvement comes from the opening geometry while the remainder comes from increasing the distance between the edge of tether 44 and the side of the openings.

Figure 5:
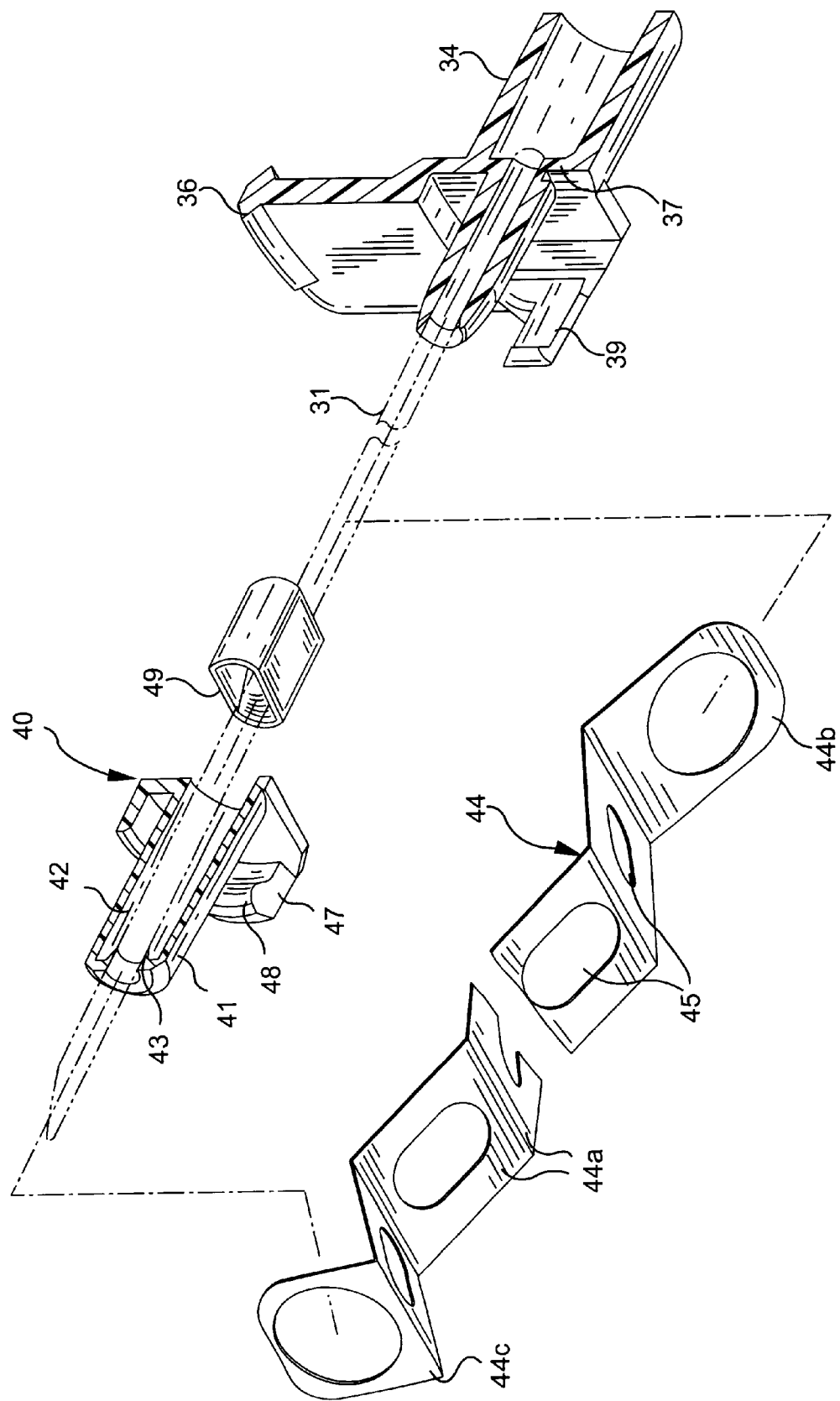
FIG. 5 is an exploded bottom perspective view in partial cross section and partially in phantom of a portion of the needle shield, tether and the needle hub illustrating one method of connecting the tether to the needle shield and the needle hub.
Figure 6:
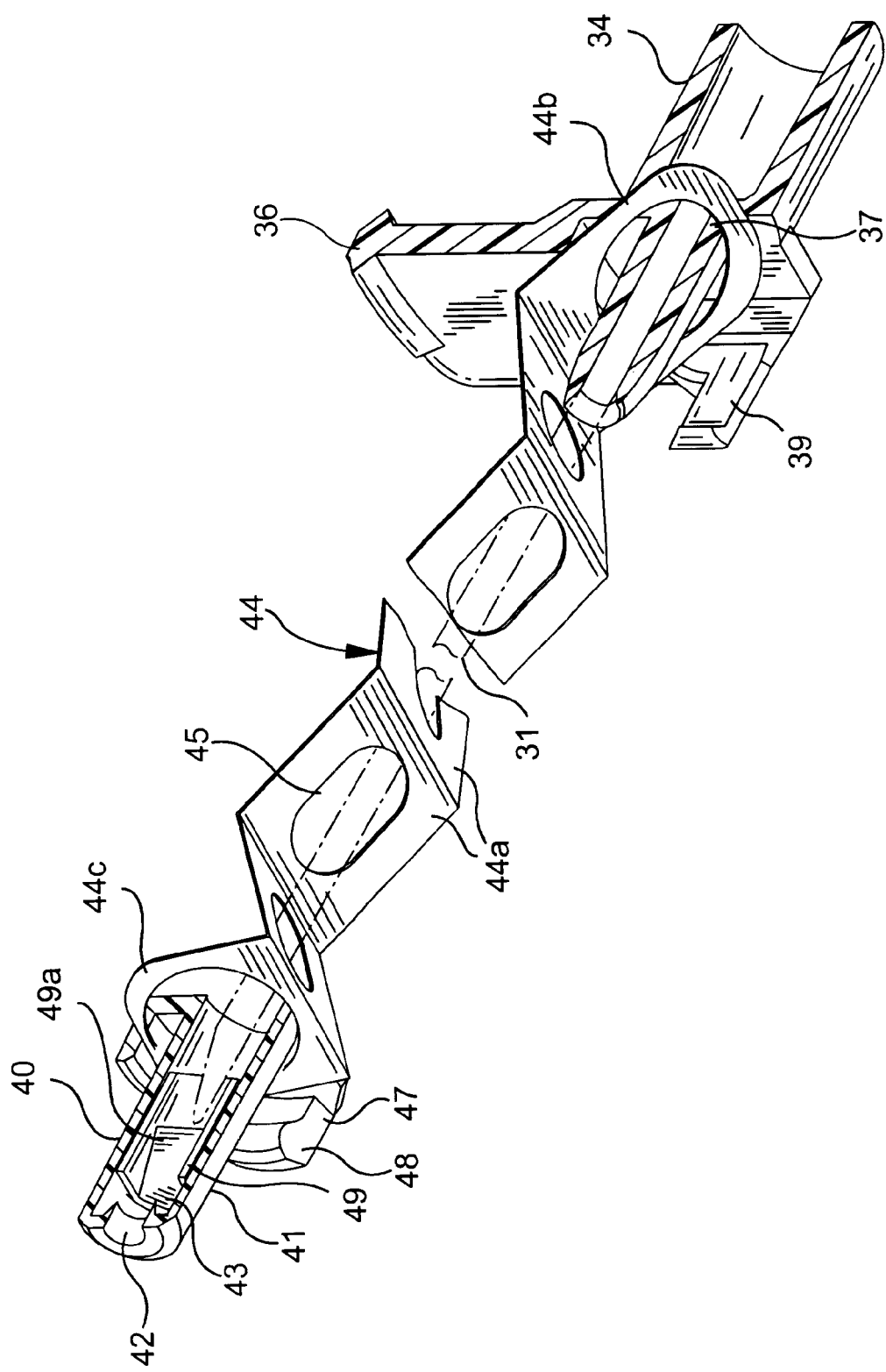
FIG. 6 is a bottom perspective view in partial cross section and partially in phantom of a portion of the needle shield, tether and the needle hub illustrating one method of connecting the tether to the needle shield and the needle hub.
Figure 10:
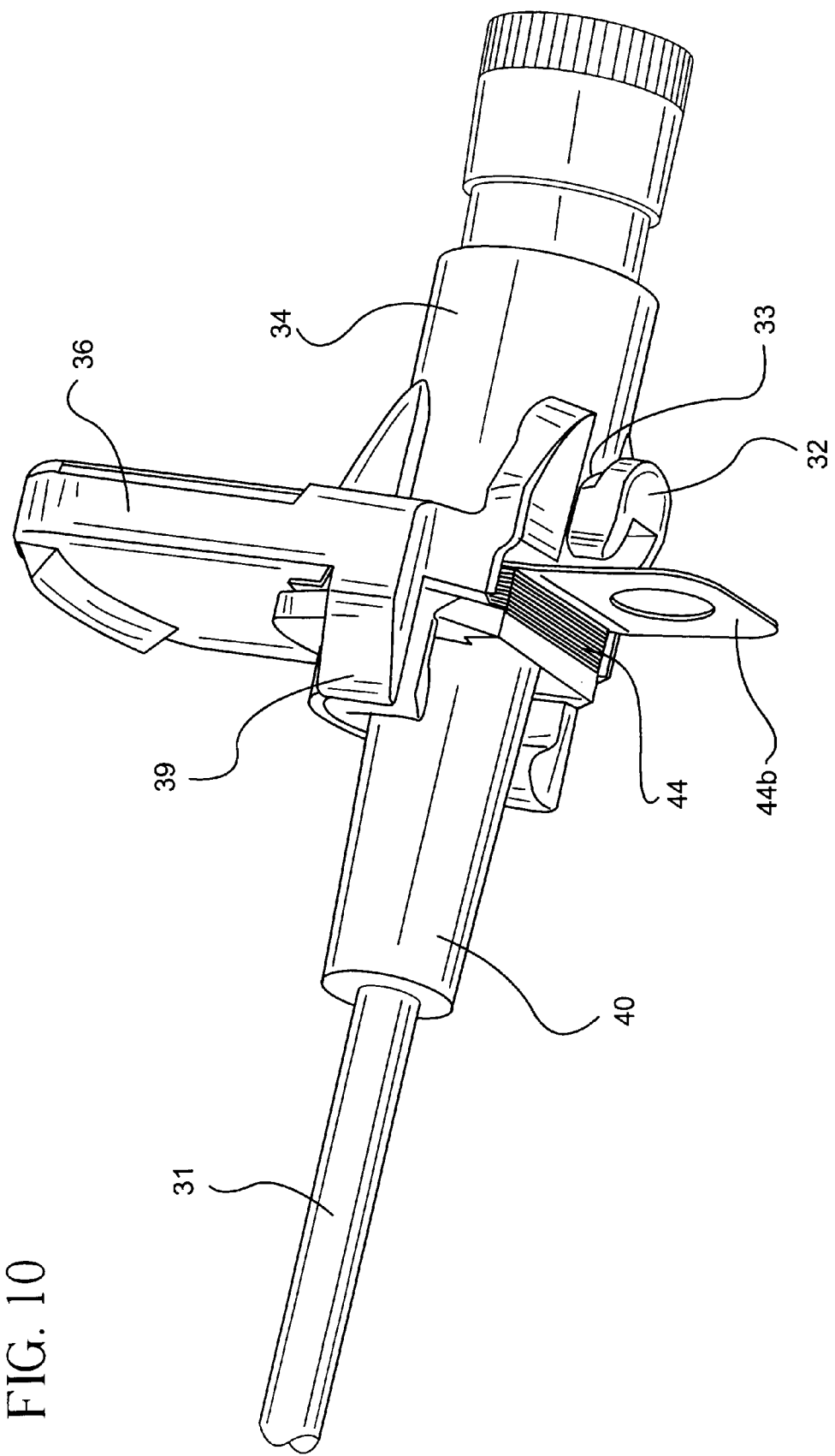
FIG. 10 is a bottom perspective view of the needle shield, tether and the needle hub where the needle shield is adjacent to the needle hub illustrating a second method of connecting the tether to the needle hub with the proximal most pleat of the tether disengaged from the needle hub.
Figure 11:
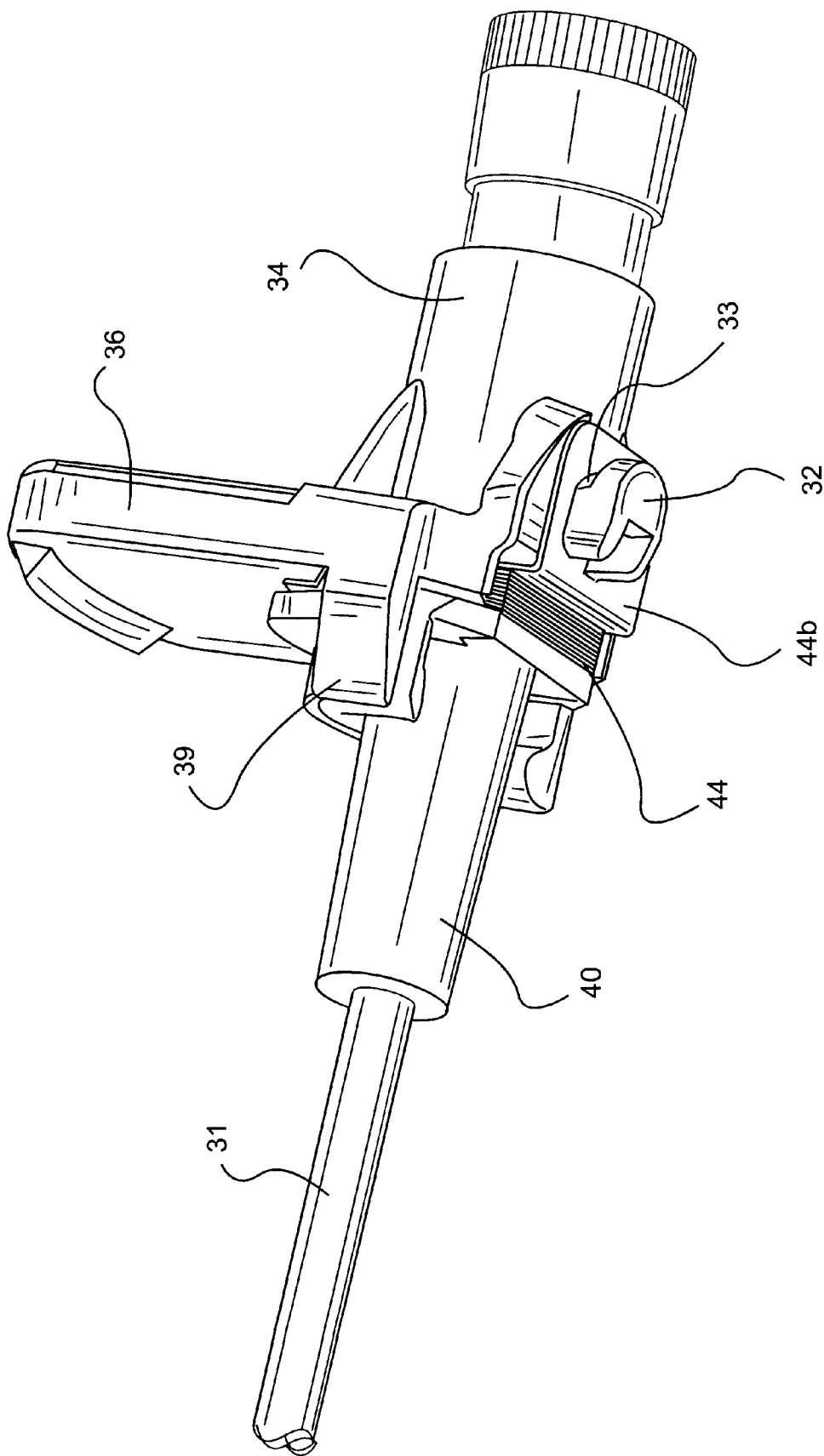
FIG. 11 is a bottom perspective view of the needle shield, tether and the needle hub where the needle shield is adjacent to the needle hub illustrating a second method of connecting the tether to the needle hub with the proximal most pleat of the tether engaged with the needle hub.
Figure 12:
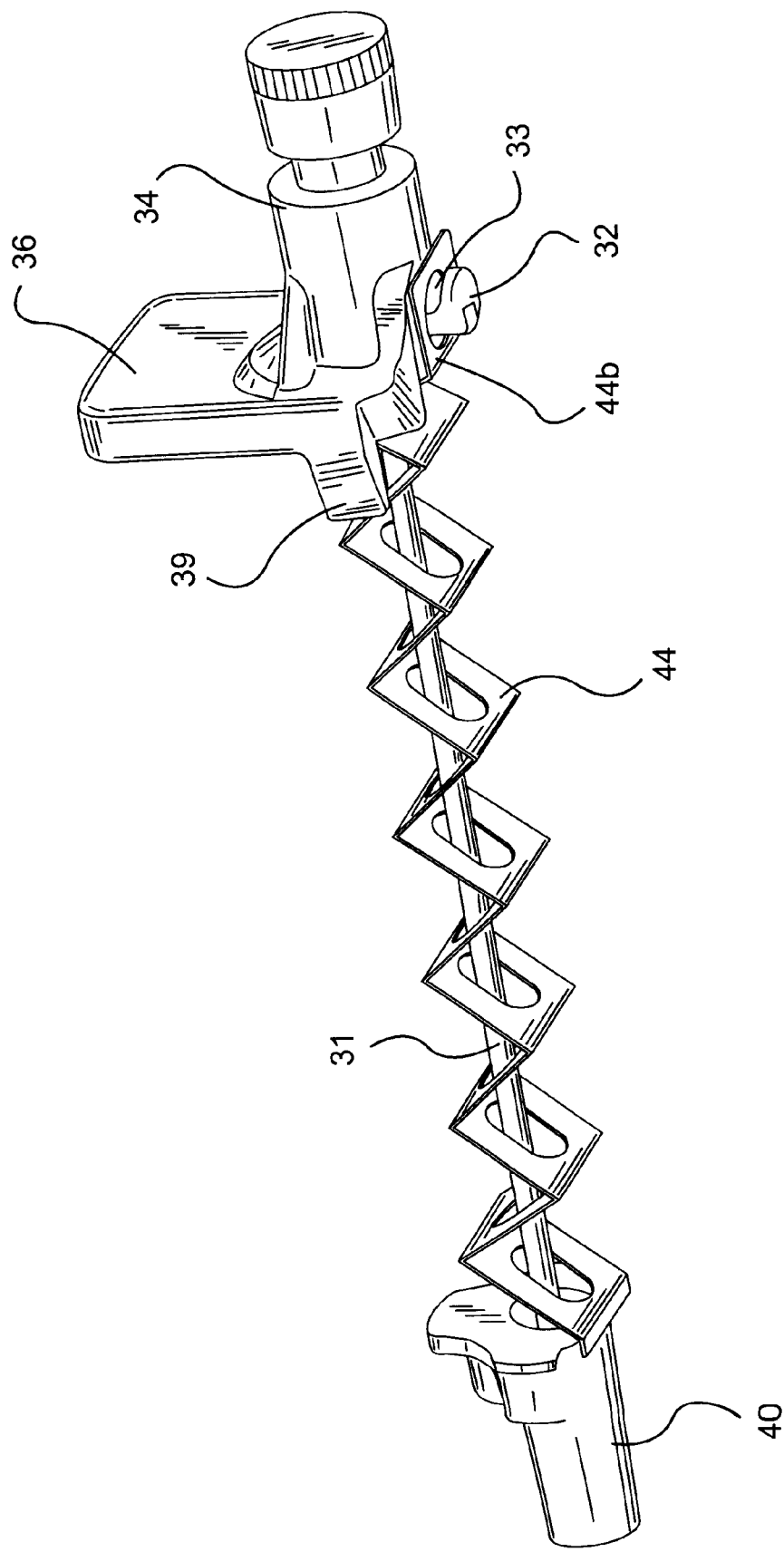
FIG. 12 is a bottom perspective view of introducer needle assembly with the needle shield and tether of this invention after the needle has been withdrawn from the catheter into the needle shield and the needle shield has been removed from the catheter hub illustrating a second method of connecting the tether to the needle hub.

Tether 44 can be connected to needle hub 34 and needle shield 40 by any standard means, such as by an adhesive or by heat-sealing. Preferably, tether 44 is connected to needle hub 34 and needle shield 40 through mechanical engagement as well as by an adhesive. For example, a slot 37 may be formed along a distal portion of needle hub 34 where one end of tether 44 can be placed. Slot 37 thus provides an edge along which a proximal pleat 44b of tether 44 can mechanically engage needle hub 34 to prevent tether 44 from being removed from needle hub 34 during use. See FIGS. 5 and 6. Alternatively, a radially extending button 32 defining a slot 33 therein can be formed along a bottom portion of needle hub 34. One end of tether 44 can be located about button 32 so that slot 33 provides an edge along which a proximal pleat 44b can mechanically engage needle hub 34. See FIGS. 10–12. As to main body portion 41, a distal pleat 44c can be looped around main body portion 41 of needle shield 40 to prevent tether 44 from being removed from main body portion 41 during use. See FIGS. 5 and 6. Although it is preferred to have tether 44 connected to needle hub 34 and needle shield 40 as described above, it is to be understood that other well known methods for joining two pieces together may be used.

The combination of the material for tether 44, the pleated configuration of tether 44, and the specific connection of distal pleat 44c to main body portion 41 causes the longitudinal axis of main body portion 41 to form an oblique angle with respect to introducer needle 31 when tether 44 is fully extended. This helps to ensure that the sharp distal tip of introducer needle 31 remains trapped inside needle shield 40 if introducer needle 31 were to be subsequently moved distally with respect to main body portion 41 and prevents the sharp distal tip of introducer needle 31 from being reexposed after use.

In order to place catheter 21 into a patient's blood vessel, the clinician substantially longitudinally aligns introducer needle 31 and catheter 21 with the target blood vessel. The bevel defining the sharp distal tip of introducer needle 31 should be facing substantially away from the skin surface during venipuncture. The clinician inserts introducer needle 31 and catheter 21 at a shallow angle, preferably less than about 35 degrees, into the skin so that the sharp distal tip of introducer needle 31 enters the target blood vessel. The clinician then preferably observes a blood flashback in the flashback chamber.

After confirming placement of introducer needle 31 and catheter 21 in the target blood vessel, the clinician advances catheter 21 distally axially along introducer needle 31 into position in the blood vessel. After proper placement of catheter 21 is achieved, the clinician places a finger from her other hand on the patient's skin over the blood vessel distal of the distal end of catheter 21 and the sharp distal tip of introducer needle 31. By placing her finger on the patient's skin and applying sufficient pressure on the skin, the clinician thereby minimizes blood flow through catheter 21. The clinician then withdraws introducer needle 31 from catheter 21 by pulling needle hub 34 in a proximal direction. Once sharp distal tip of introducer needle 31 is located within main body portion 41 of needle shield 40, continued proximal movement of needle hub 34 will result in a force sufficient to overcome the force holding fingers 47 to catheter adapter 24 so that main body portion 41 can be removed from catheter adapter 24. Thereafter, the clinician may attach any desired fluid-handling device to side port 25, if a ported catheter is used, or to catheter adapter 24, if a straight catheter is used, and commence the planned treatment. Main body portion 41 of needle shield 40 with the sharp distal tip of introducer needle 31 shielded therein may then be disposed of according to the facility's disposal protocol.

Thus, it is seen that an introducer needle assembly having a needle shield is provided that positively connects the needle shield to the introducer needle assembly to prevent the needle shield from being advanced distally past the distal end of the introducer needle, is compact, simple and easy to use, requires no special features or technique to be operative and is ergonomically comfortable for the clinician to use.

We claim:

1. A catheter and introducer needle assembly, comprising:
   a catheter having a proximal end and distal end;
   a catheter hub in fluid communication with the catheter and having a proximal end and a distal end connected to the proximal end of the catheter;
   an introducer needle disposed in the catheter and having a proximal end and a distal end;

a needle hub in fluid communication with the needle and having a proximal end and a distal end connected to the proximal end of the catheter;

a needle shield having a proximal end and a distal end removably connected to the catheter hub, the needle shield defining a longitudinally extending passageway therethrough with the introducer needle extending through the longitudinally extending passageway; and a pleated tether connecting the needle hub to the needle shield to prevent unwanted proximal movement of the introducer needle with respect to the needle shield wherein the pleated tether is formed from a plurality of pleats each defining a hole therein through which the introducer needle extends wherein each hole defines a longitudinal dimension and a radial dimension wherein the radial dimension is less than the longitudinal dimension.

2. The catheter and needle assembly of claim 1 wherein the hole has a racetrack configuration.

3. The catheter and needle assembly of claim 1 wherein the hole has an elliptical configuration.

4. The catheter and needle assembly of claim 1 wherein the hole has a generally rectangular configuration.

5. The catheter and needle assembly of claim 1 wherein each hole is at least 0.030 inches apart.

6. The catheter and needle assembly of claim 5 wherein the longitudinal dimension is 0.138 inches.

7. The catheter and needle assembly of claim 6 wherein the radial dimension is no greater than 0.108 inches.

8. A needle assembly, comprising:

a needle having a proximal end and a distal end;

a needle hub in fluid communication with the needle and having a proximal end and a distal end connected to the proximal end of the catheter;

a needle shield disposed about the needle;

a pleated tether connecting the needle hub to the needle shield wherein the pleated tether is formed from a plurality of pleats each defining a hole therein through which the needle extends wherein each hole defines a longitudinal dimension and a radial dimension wherein the radial dimension is less than the longitudinal dimension.

9. The catheter and needle assembly of claim 8 wherein the hole has a racetrack configuration.

10. The catheter and needle assembly of claim 8 wherein the hole has an elliptical configuration.

11. The catheter and needle assembly of claim 8 wherein the hole has a generally rectangular configuration.

12. The catheter and needle assembly of claim 8 wherein each hole is at least 0.030 inches apart.

13. The catheter and needle assembly of claim 12 wherein the longitudinal dimension is 0.138 inches.

14. The catheter and needle assembly of claim 13 wherein the radial dimension is no greater than 0.108 inches.

* * * * *